(12) United States Patent
Salaet Ferré et al.

(10) Patent No.: US 9,157,166 B2
(45) Date of Patent: Oct. 13, 2015

(54) PROCESS FOR PREPARING THE CRYSTALLINE FORM A OF (2-[3-CYANO-4-(2-I-BUTOXY)PHENYL]-4-METHYL-5-THIAZOLE-CARBOXYLIC ACID (FEBUXOSTAT)

(75) Inventors: Josep Salaet Ferré, Barcelona (ES); Francisco Marquillas Olondriz, Barcelona (ES)

(73) Assignee: INTERQUIM, S.A., Sant Cugat del Valles (ES)

( * ) Notice: Subject to any disclaimer, the term of this patent is extended or adjusted under 35 U.S.C. 154(b) by 448 days.

(21) Appl. No.: 13/809,851

(22) PCT Filed: Jul. 13, 2011

(86) PCT No.: PCT/EP2011/061905
§ 371 (c)(1),
(2), (4) Date: Feb. 12, 2013

(87) PCT Pub. No.: WO2012/007486
PCT Pub. Date: Jan. 19, 2012

(65) Prior Publication Data
US 2013/0145983 A1 Jun. 13, 2013

(30) Foreign Application Priority Data
Jul. 13, 2010 (ES) .................................. 201031060

(51) Int. Cl.
C30B 7/00 (2006.01)
C30B 7/08 (2006.01)
C07D 277/56 (2006.01)
C30B 29/54 (2006.01)

(52) U.S. Cl.
CPC ................ C30B 7/08 (2013.01); C07D 277/56 (2013.01); C30B 29/54 (2013.01)

(58) Field of Classification Search
CPC .............. C30B 7/00; C30B 7/02; C30B 7/08; C30B 7/14; C30B 29/54
See application file for complete search history.

(56) References Cited

FOREIGN PATENT DOCUMENTS

| CN | 101139325 A | | 3/2008 |
|---|---|---|---|
| CN | 101812035 | * | 8/2010 |
| EP | 1 020 454 A1 | | 7/2000 |

OTHER PUBLICATIONS

International Search Report, dated Aug. 16, 2011, issued in PCT/EP2011/061905.
Letter Regarding Filing of Arguments in Response to the ISR/WO dated Aug. 16, 2011, filed in PCT/EP2011/061905.
Written Opinion of the International Searching Authority, dated Aug. 16, 2011, issued in PCT/EP2011/061905.

* cited by examiner

*Primary Examiner* — Robert M Kunemund
(74) *Attorney, Agent, or Firm* — Birch, Stewart, Kolasch & Birch, LLP

(57) ABSTRACT

The invention relates to a novel process for preparing the crystalline from A of febuxostat by crystallization in a solvent selected from ethyl acetate, isopropyl acetate or ethyl formiate.

5 Claims, 2 Drawing Sheets

PROCESS FOR PREPARING THE CRYSTALLINE FORM A OF (2-[3-CYANO-4-(2-I-BUTOXY)PHENYL]-4-METHYL-5-THIAZOLE-CARBOXYLIC ACID (FEBUXOSTAT)

The present invention relates to a process for preparing the crystalline form A of febuxostat (2-[3-cyano-4-(2-i-butoxy) phenyl]-4-methyl-5-thiazole-carboxylic acid). Febuxostat is an inhibitor of xanthine oxidase that is indicated in the treatment of hyperuricemia. Its structural formula is as follows:

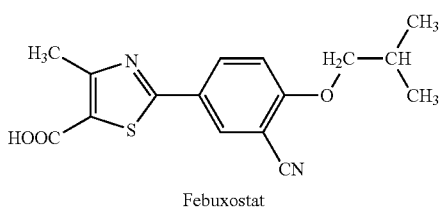 [SMILES: Cc1nc(-c2ccc(OCC(C)C)c(C#N)c2)sc1C(=O)O]

Febuxostat

BACKGROUND ART

EP1020454 describes polymorphic forms A, B, C, D and G of febuxostat as well as process for their preparation by crystallization of febuxostat in a methanol/water mixture, depending on concentration and temperature conditions. The process also includes the preparation of an amorphous form. The six different polymorphs may be produced using the same phase diagram.

However, by performing different assays the authors of the present invention have found that the preparation of form A according to the processes described in EP1020454 is hardly reproducible and, in addition, contamination of other forms may occur or undesired forms may be obtained.

Thus, there is a need to develop a process for preparing the crystalline form A of febuxostat that is capable of providing a good yield and high purity.

SUMMARY OF THE INVENTION

The invention provides a novel industrial process for the preparation of crystalline form A of febuxostat with high yield and high purity, because of using a sole non-toxic solvent with a low boiling point.

By using a sole solvent for preparing form A under certain conditions, form A is consistently obtained since its preparation does not depend on the proportion of different solvents.

Unlike the above prior art patent, the temperature and drying conditions in the process of the present invention do not affect the characteristics of the crystalline form obtained, since form A is consistently produced by using the solvents of the invention.

DETAILED DESCRIPTION OF THE INVENTION

The object of the present invention is to provide a process for preparing the crystalline form A of febuxostat, comprising the following steps:
a) Dissolving febuxostat in a solvent selected from the group consisting of ethyl acetate, isopropyl acetate and ethyl formiate in a proportion from 5 to 60 ml of solvent per gram of solute, at a temperature between 50° C. and boiling temperature of the solution;
b) Forming the crystals by keeping the solution from step a) at a temperature between 45° C. and boiling temperature of the mixture over a period of 1-24 hours, when the solvent is ethyl acetate or isopropyl acetate; and
c) Isolating the crystalline form A of febuxostat, by cooling at room temperature, from
c.1.) the suspension from step b), and thereby standing over a period of 3-15 hours; or
c.2.) the solution from step a), without going through step b), by stirring over a period of 3-24 hours, when the solvent is ethyl formiate;
followed by filtration and drying.

In a preferred embodiment, in step a), the proportion of solvent per gram of solute is from 10 to 50 ml.

In another preferred embodiment, in step b), the crystallization period is from 3 to 15 hours.

In another preferred embodiment, in step c.1.), the period is from 8 to 10 hours.

In another preferred embodiment, in step c.2.), the stirring period is from 3 to 15 hours.

EXAMPLES

Example 1

Preparation of form A of 2-[3-cyano-4-(2-i-butoxy) phenyl]-4-methyl-5-thiazole-carboxylic acid (Febuxostat) in ethyl acetate To 10.0 g of 2-[3-cyano-4-(2-i-butoxy)phenyl]-4-methyl-5-thiazole-carboxylic acid, 100 ml of ethyl acetate were added. The mixture was heated under reflux until complete dissolution. The solution was cooled to 60° C., and the presence of a precipitate was observed during cooling. The mixture was heated at 65° C. and kept at this temperature for 3 hours. Then, it was cooled at room temperature for 10 h, and the solid was filtered. The resulting product was dried under vacuum at 65° C. for 15 h. 7.9 g of febuxostat as pure form A were obtained.

Example 2

Preparation of form A of 2-[3-cyano-4-(2-i-butoxy) phenyl]-4-methyl-5-thiazole-carboxylic acid (Febuxostat) in isopropyl acetate To 10.0 g of 2-[3-cyano-4-(2-i-butoxy)phenyl]-4-methyl-5-thiazole-carboxylic acid, 400 ml of isopropyl acetate were added. The mixture was heated under reflux until complete dissolution. The solution was cooled to 60° C., and the presence of a precipitate was observed during cooling. The mixture was heated at 65° C. and kept at this temperature for 3 h. Then, it was cooled at room temperature for 10 h, and the solid was filtered. The resulting product was dried under vacuum at 65° C. for 15 h. 7.9 g of febuxostat as pure form A were obtained.

Example 3

Preparation of form A of 2-[3-cyano-4-(2-i-butoxy)phenyl]-4-methyl-5-thiazole-carboxylic acid (Febuxostat) in ethyl formiate To 2.0 g of 2-[3-cyano-4-(2-i-butoxy)phenyl]-4-methyl-5-thiazole-carboxylic acid, 90 ml of ethyl formiate were added. The mixture was heated under reflux and slowly cooled to room temperature. Then, it was kept under stirring for 15 h at room temperature. The suspension was filtered. The resulting product was dried at 65° C. for 15 h and 1.14 g of febuxostat as pure form A were obtained.

Figure 1:
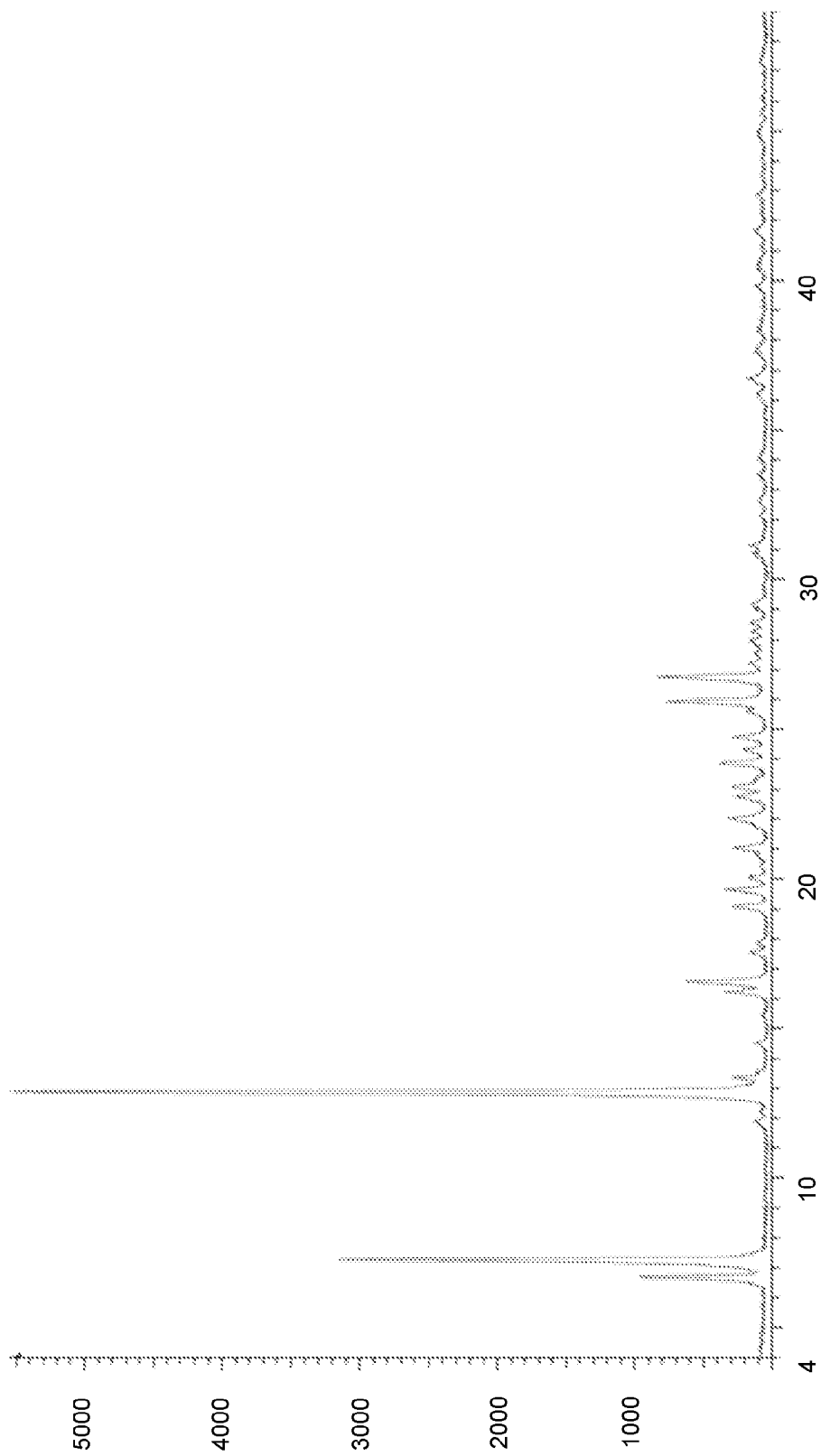
FIG. 1 shows the X-ray powder diffraction pattern of crystalline form A of febuxostat produced by the process of the present invention. The ordinate shows the intensity value expressed on a linear counting scale and the abscissa shows the diffraction angle (2θ°).
Figure 2:
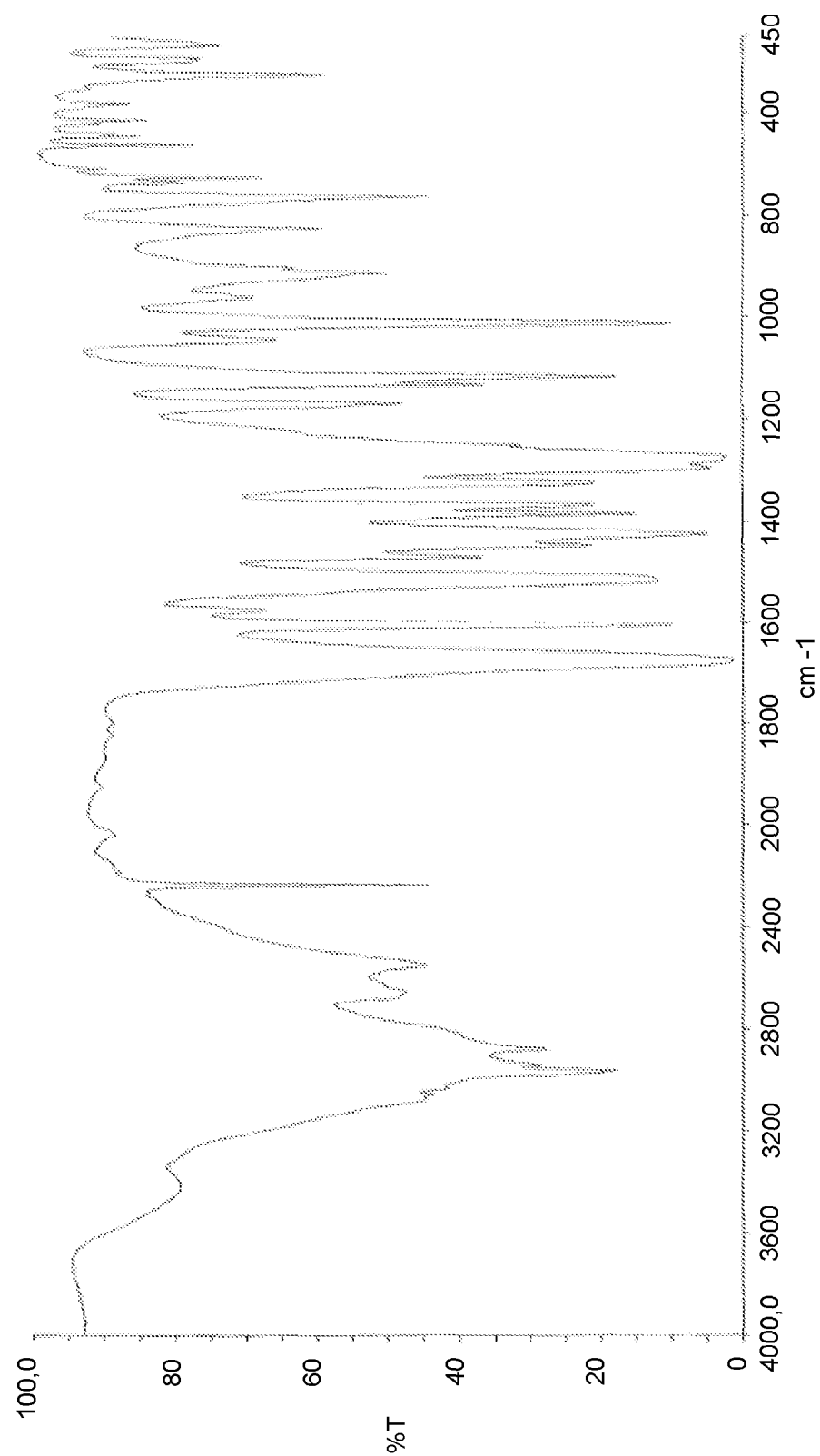
FIG. 2 shows the IR spectrum recorded on KBr tablet of crystalline form A of febuxostat produced by the process of the present invention.

X-ray diagram (FIG. 1) and IR spectrum (FIG. 2) of any one of the samples prepared in Examples 1-3 were consistent with those reported in prior art.

The invention claimed is:

1. A process for preparing the crystalline form A of febuxostat, comprising the following steps:
   a) Dissolving febuxostat in a solvent selected from the group consisting of ethyl acetate, isopropyl acetate and ethyl formiate in a proportion from 5 to 60 ml of solvent per gram of solute, at a temperature between 50° C. and boiling temperature of the solution;
   b) Forming the crystals by keeping the solution from step a) at a temperature between 45° C. and boiling temperature of the mixture over a period of 1-24 hours, when the solvent is ethyl acetate or isopropyl acetate; and
   c) Isolating the crystalline form A of febuxostat, by cooling at room temperature, from
      c.1.) the suspension from step b), and thereby standing over a period of 3-15 hours; or
      c.2.) the solution from step a), without going through step b), by stirring over a period of 3-24 hours, when the solvent is ethyl formiate;
   followed by filtration and drying.

2. The process according to claim 1, step a), wherein the proportion of solvent per gram of solute is from 10 to 50 ml.

3. The process according to claim 1, step b), wherein the crystallization period is from 3 to 15 hours.

4. The process according to claim 1, step c.1), wherein the period is from 8 to 10 hours.

5. The process according to claim 1, step c.2), wherein the stirring period is from 3 to 15 hours.

* * * * *